United States Patent [19]

Cox et al.

[11] Patent Number: 4,923,681
[45] Date of Patent: May 8, 1990

[54] HIGH VELOCITY HOT AIR STERILIZATION DEVICE WITH CONTROLLER

[75] Inventors: M. Keith Cox, Dallas, Tex.; William E. Davidson, Scarborough, Canada

[73] Assignee: ArcherAire Industries, Inc., Dallas, Tex.

[21] Appl. No.: 112,227

[22] Filed: Oct. 22, 1987

Related U.S. Application Data

[63] Continuation-in-part of Ser. No. 915,116, Oct. 3, 1986, abandoned.

[51] Int. Cl.⁵ .............................................. G05B 17/02
[52] U.S. Cl. ..................................... 422/116; 219/400; 219/492; 219/497; 323/236; 422/109; 422/119; 422/124
[58] Field of Search ............... 422/116, 108, 109, 1-2, 422/117, 119, 124, 28; 219/400, 497, 492; 323/235, 236

[56] References Cited

U.S. PATENT DOCUMENTS

| | | | |
|---|---|---|---|
| 3,721,525 | 3/1973 | Hortig et al. | 422/1 |
| 3,801,278 | 4/1974 | Wagner et al. | 422/300 X |
| 3,958,936 | 5/1976 | Knight, Jr. | 422/1 |
| 4,003,703 | 1/1977 | Montgomery, Jr. et al. | 422/116 X |
| 4,067,691 | 1/1978 | McGady et al. | 422/1 |
| 4,167,663 | 9/1979 | Granzow, Jr. et al. | 219/497 |
| 4,188,528 | 2/1980 | Wierzchowski et al. | 219/492 X |
| 4,203,947 | 5/1980 | Young et al. | 422/116 |
| 4,261,950 | 4/1981 | Bainbridge et al. | 422/112 X |
| 4,277,671 | 7/1981 | Mori et al. | 219/497 X |
| 4,294,804 | 10/1981 | Baran | 422/116 |
| 4,309,381 | 1/1982 | Chamberlain et al. | 422/116 |
| 4,317,975 | 3/1982 | Mizukawa et al. | 323/235 X |
| 4,334,147 | 8/1982 | Payne | 219/497 |
| 4,447,399 | 5/1984 | Runnells et al. | 422/109 X |
| 4,455,478 | 6/1984 | Guibert | 219/400 |
| 4,457,892 | 7/1984 | Young | 422/117 X |
| 4,465,924 | 8/1984 | Payne | 219/492 |
| 4,486,648 | 12/1984 | Grasso | 219/492 X |
| 4,506,146 | 3/1985 | Rice et al. | 323/235 X |
| 4,582,076 | 4/1986 | Prat | 422/28 X |
| 4,604,517 | 8/1986 | Barry | 323/235 X |
| 4,636,619 | 1/1987 | Sugimori | 323/235 X |
| 4,710,350 | 12/1987 | Petersen | 422/109 X |
| 4,745,262 | 5/1988 | Larsen | 219/497 X |
| 4,777,350 | 10/1988 | Crockett et al. | 219/497 |
| 4,779,036 | 10/1988 | Shinoda | 323/236 |
| 4,791,545 | 12/1988 | Hinckley | 323/235 X |

Primary Examiner—Robert J. Hill, Jr.
Assistant Examiner—Amalia L. Santiago
Attorney, Agent, or Firm—Hubbard, Thurman, Turner, Tucker & Harris

[57] ABSTRACT

An automatically controlled recirculating high velocity hot air sterilization device includes a housing having a sterilization chamber with a temperature sensor mounted therein, a hot air plenum including a blower in fluid communication with a heating element and sterilization chamber for inputting hor air into and receiving hot air from the sterilization chamber for recirculation, and a control chamber having a temperature sensing circuit connected to the temperature circuit for producing electrical inputs representative of the sterilization chamber temperature, power circuits connected to the heating element and blower, a controller connected to the temperature sensing circuit for monitoring the temperature, and to the heating element and blower circuits for controlling their operation, and a control panel including cycle selection switches for operation, an on/off switch, and temperature and timer/error displays. The controller is designed for monitoring the cycle selection switches and on/off switch, for controlling operation of the heating element, blower and timer for the cycle selected, for monitoring the temperature, for starting the timer when the temperature rises to the required temperature, for restarting the timer should the temperature fall below the required temperature during a cycle, for shutting down the device when a catastrophic failure occurs and for outputting an error signal together with problem information for display.

11 Claims, 6 Drawing Sheets

HIGH VELOCITY HOT AIR STERILIZATION DEVICE WITH CONTROLLER

CROSS-REFERENCE TO RELATED APPLICATION

This application is a continuation-in-part of pending U.S. application Ser. No. 915,116 filed on Oct. 3, 1986 now abandoned and entitled: "Recirculating High Velocity Hot Air Sterilization Device".

BACKGROUND OF THE INVENTION

1. Field of the Invention

The present invention relates to a device and process for the sterilization and depyrogenation of dental and surgical metal instruments. The invention relates, more particularly, to an automatically controlled device for the rapid, inexpensive and non-corrosive sterilization and depyrogenation of dental and surgical metal instruments.

2. Description of the Prior Art

In every health profession, the guiding principle ". . . do good, but do no harm" is as valid today as in the ancient Greece of its author, Hippocrates. Over the years, the second part of this motto was directed at the patient while treatment-related hazards to the practitioner's health were either discounted or accepted stoically. In dentistry, the simplistic attitude that patients—not professionals acquire treatment-related diseases is giving way to the more realistic concept that operatory personnel are the main targets of viral and bacterial agents of infections.

To demonstrate the central position of dentists in the acquisition and broadcast of nosocomial infectious disease, their rate of hepatitis B infection is four-fold higher than that of the general public. If the dentist is male, he can pass the disease by sexual activity to his wife. If she, or female operatory personnel, incubate the virus during pregnancy, their newborn children have a 90% chance of becoming lifelong carriers of the virus and a 53% chance of dying from liver cancer. Male or female, dental personnel harboring hepatitis B virus can pass the disease to patients, especially via blood exiting the finger through cuts.

The recent dramatic rise in the spread of infectious diseases in the United States has resulted in an acute awareness of the potentially grave danger of transmission to health care professionals in general. As noted above, dentists and dental auxiliaries occupy a central position in the acquisition and broadcast of nosocomial infectious disease. The risk, however, extends beyond dentists and dental auxiliaries to the crossover contamination from patient to patient.

For example, it is estimated that there are 200,000 new cases of hepatitis B in the U.S. each year with nearly 1 million chronic carriers. Since 1974, there has been a 234% increase in reported cases of Herpes Simplex II and a 40,350% increase in AIDS cases. Add to these the diseases that can frequently be transmitted, such as gonorrhea, infectious mononucleosis, measles, pneumonia, tetanus, amoebic dysentery and the highly resistant organisms that are reaching the United States from foreign countries, and a frightening scenario emerges.

Recent legal decisions have placed the burden of proof of proper sterilization procedures on the dental office where the possibility of suspected transmission of infection exists. It follows that malpractice insurance carriers may soon require strict adherence to effective and accepted sterilization procedures.

The solution to the problem of contamination with infectious disease in the dental office from patient to dental personnel and from patient to patient is to ensure the complete sterilization and depyrogenation (killing all forms of microbial life: viral and bacterial pathogens including spores) of all instruments.

In the dental office environment, there are several currently accepted means of sterilization. All of the systems currently employed, as discussed below, lack the capability of rapid sterilization of instruments between patients to allow the immediate reuse of the instruments.

The first method of sterilization is known as cold solution sterilization. Cold solution sterilization requires 20 to 30 minutes to disinfect and 10 hours to sterilize (if the solution is fresh and mixed to proper strength). Procedural problems involved with cold solution sterilization are as follows: many currently available solutions will discolor the skin on contact; most available solutions have an offensive odor; dental instruments will rust if they are left in the solutions over an extended period of time; and instruments are often placed in the solution haphazardly with no record of how long they remain. Other limitations concerning the cold solution sterilization system include the fact that the required solutions are expensive and must constantly be replenished.

The second method of sterilization involves the utilization of steam heat. Steam heat sterilization requires 30 to 60 minutes to sterilize. Procedural problems involved with steam heat sterilization are as follows: a central sterilization area is required and a large piece of expensive equipment which can be hazardous to operating personnel is required. Other limitations concerning steam heat sterilization include the fact that the method corrodes, rusts and dulls instruments—particularly where such instruments are of a carbon steel construction.

The third method of sterilization involves the use of alcohol steam. Alcohol steam requires a minimum of 30 minutes to achieve sterilization. Procedural problems involved with alcohol steam sterilization are as follows: a central sterilization area is required; sterilization usually requires the use of "wrapped packs" which necessitate an increase in the number of instruments needed by an office; and the use of "wrapped packs" also lends itself to careless techniques in that packs are often broken into to retrieve one needed instrument if complete packs of all instruments are not available. Other limitations concerning alcohol steam sterilization include the fact that alcohol steam also corrodes instruments, but not to the same degree as steam heat. Additionally, alcohol steam contains formaldehyde—the presence of which constitutes a potential health hazard. Accordingly, purging systems are typically required to exhaust the alcohol steam from the sterilizer cabinet each time its access door is opened.

The fourth method of sterilization involves the use of dry heat. Dry heat sterilization conventionally requires a minimum of 60 minutes to achieve sterilization. With the exception of the purging requirements associated with the presence of formaldehyde, the problems involved with dry heat sterilization are essentially the same as discussed with regard to alcohol steam sterilization since wrapped packs are used. Additionally, however, the lack of uniform sterilizing heat distribution, and a corresponding non-uniform temperature pattern within the sterilizing cabinetry, render the validation of the sterilization process somewhat difficult.

The fifth method of sterilization involves the use of ethylene oxide gas. The size, expense and sophistication of this process and the necessary equipment, however, limit its use to commercial large volume sterilization.

The sixth method of sterilization involves the use of heat transfer with glass beads, sand, glass, ball bearings and other similar items being used as a heat-transfer medium. Heat transfer sterilization requires 10 seconds at 450° to achieve sterilization. This method has no known procedural problems. A major limitation concerning heat transfer sterilization, however, is the fact that a small unit is used which is suitable only for small endodontic files, broaches and other similar items.

Among the currently employed sterilization systems, the heat transfer system is the only one with the capability of rapid sterilization of instruments between patients and its small capacity limits its use in the dental office.

Thus, a need exists in the art for a rapid, safe, inexpensive and non-corrosive sterilization method and device that provides for the automatic sterilization and depyrogenation of procedural instruments in health care facilities and especially the dental office thereby minimizing the human error factors attending the use of known sterilization devices.

SUMMARY OF THE INVENTION

The device for the automatic sterilization and depyrogenation of dental and surgical metal instruments of the present invention avoids the above-mentioned disadvantages which are characteristic of the prior art. More specifically, the device of the present invention provides an automatically controlled means for the sterilization of dental and surgical metal instruments that is rapid, non-corrosive, clean, inexpensive and efficient. The device of the present invention is an automatically controlled dry-heat sterilizer that utilizes the speed of heat transfer principles in a unit large enough to accommodate dental instruments and other small surgical instruments. The device is also useful for the sterilization and depyrogenation of dental and surgical implants.

The sterilization device of the present invention has high heat transfer efficiency and reduces the time required to sterilize dental and surgical metal instruments over that required by conventional sterilization devices. The sterilization device of the present invention provides complete sterilization and depyrogenation, utilizing a process in which deturbulized air, moving at, preferably, 1500 to 3000 feet per minute, is heated to a sterilizing temperature of, preferably, 350° to 400° F.

The sterilization device operation is under the control of a controller. The controller includes two timed operating cycle selections. A first cycle selection provides for the operation of the device for a first preselected time, for example, three minutes, continuously at a temperature of about 375° F. for sterilizing unwrapped instruments. While a second cycle selection provides for operation of the device for a second preselected time, and temperature for sterilizing instruments requiring additional time such as, for example, wrapped instruments, excessively bulky instruments, or a large quantity load. Any interruptions of the operation of the device or a drop in temperature during operation restarts the timer.

The controller also features: a solid state display; a monitor for detecting system operating failures; a temperature reading means for continuous temperature reading; a proportional heat control means for the heating element; relays responsive to on/off switch inputs for controlling fan and heater on/off operations; an audible alarm for alerting an operator as to system operating status; a timer for providing an accurate time base; and an input means for operator input including on/off operation.

The sterilization device of the present invention provides for instrument sterilization between treatment of each patient thereby eliminating the greatest source of contamination from patient to personnel as well as cross contamination from patient to patient.

The sterilization device of the present invention and its variations may be used in dental offices, medical offices and clinics particularly where minor surgical procedures are performed; in oral surgery offices; in hospitals and other health care facilities; in emergency rooms; in Dental, Medical and Veterinary Medical Schools; in schools of Dental Hygiene; in schools of Medical Technology; in schools of Physical Therapy; in Military Health Care Facilities; and, in other environments where individuals could be subjected to contamination or cross infection including, but not limited to, ear piercing, electrolysis and skin care.

It is an object of the present invention to provide a device for the sterilization and depyrogenation of metal dental instruments that is 10 to 20 times faster than any other currently employed system of sterilization in the dental office; completely safe to operating personnel; durable and lasts the lifetime of a dental office with only the simple replacement of a fan motor or heating element; simple in operation; more inexpensive than other types of sterilization devices; less harmful to instruments than any other types of specification; small enough for use in the operatory and does not require a central sterilization area; inexpensive enough to allow for use of multiple units placed at convenient locations where instruments are used; maintenance free; preferably insulated to protect the outside of the unit from becoming hot; and preferably constructed with external stainless steel to provide a lifetime non-corrosive surface that can be disinfected with a wipe solution.

It is another object of the present invention to provide a device that reliably provides total sterilization and depyrogenation of dental and surgical metal instruments.

It is an additional object of the present invention to provide a device for the sterilization and depyrogenation of dental and surgical metal instruments that releases no heat or odor and does not require the use or addition of chemicals.

It is a further object of the invention to provide sterilization and depyrogenation device having a controller for controlling the operation of the device, monitoring the operation of the device, and signaling operational malfunctions.

It is still a further object of the invention to provide a sterilization and depyrogenation device having multimode operation cycles for operator selection.

These and other objects are achieved by the recirculating high velocity hot air sterilization device of the present invention.

The device of the present invention includes an enclosure or housing which defines a sterilization chamber and a plenum chamber with a blower disposed in the plenum chamber. A perforated jet curtain plate is disposed within the sterilization chamber and partially defines an air supply plenum. A heating element is disposed within the air supply plenum. Means are provided for fluid communication between the outlet port of the blower, the air supply plenum, the sterilization chamber, and the intake port of the blower. The blower recirculates air throughout the device at a high temperature and a high velocity and sterilizes dental and surgical metal instruments that may be placed within the device.

The blower forces heated air upwardly through the perforations in the jet curtain plate to form within the sterilization chamber a mutually spaced series of upwardly directed high velocity heated air impingement jets. A temperature sensing means is positioned within the sterilization chamber to detect the temperature within the sterilization chamber. Positioned within the sterilization chamber in an upwardly spaced relationship with the jet curtain plate and temperature sensor is a corrugated, nonperforated air deflector plate which extends generally parallel to the jet curtain plate. The corrugated deflector plate is positioned in the path of the upwardly directed impingement jets and serves to intercept, laterally offset and rearwardly deflect such jets toward the jet curtain plate. The instruments to be sterilized are supported within a wire mesh tray which is removably positioned within the sterilization chamber between and spaced apart from the corrugated deflector plate and jet curtain plate.

Some of the upwardly directed impingement jets strike lower surface portions of the supported instruments, while other impingement jets bypass the supported instruments and impinge upon the upper deflector plate. These jets which bypass the supported instruments impinge upon the deflector plate, are laterally offset, and then are rearwardly deflected toward the supported instruments. The deflected jets impinge upon upper surface portions of the supported instruments and create a high degree of heated air turbulence adjacent thereto. The combination of high velocity heated air impinging on both sides of the instruments, and the resulting high degree of heated air turbulence, sterilizes and depyrogenates the instruments in a small fraction of the time normally required in conventional sterilizing apparatus. In addition to their jet-forming and deflecting functions, the corrugated jet curtain plate and air deflector plate additionally function in a unique manner to facilitate an extremely uniform air distribution flow within the sterilizing chamber of both the originally formed impingements jets and the rearwardly deflected impingement jets. A controller having a timer and an input/output switch means for operation cycle selection and device turn on, and a display for displaying the temperature and time remaining for completion of the selected cycle, controls the operation of the heating element and blower during the selected sterilizing cycle. The controller also monitors the temperature for restarting the timing of the cycle whenever the temperature is below the required (set) temperature. The display shows the temperature of the sterilization chamber continuously and the time remaining for completion of the selected cycle.

BRIEF DESCRIPTION OF THE DRAWINGS

In describing the invention, reference will be made to the accompanying drawings in which.

DETAILED DESCRIPTION OF THE PREFERRED EMBODIMENTS

Figure 1:
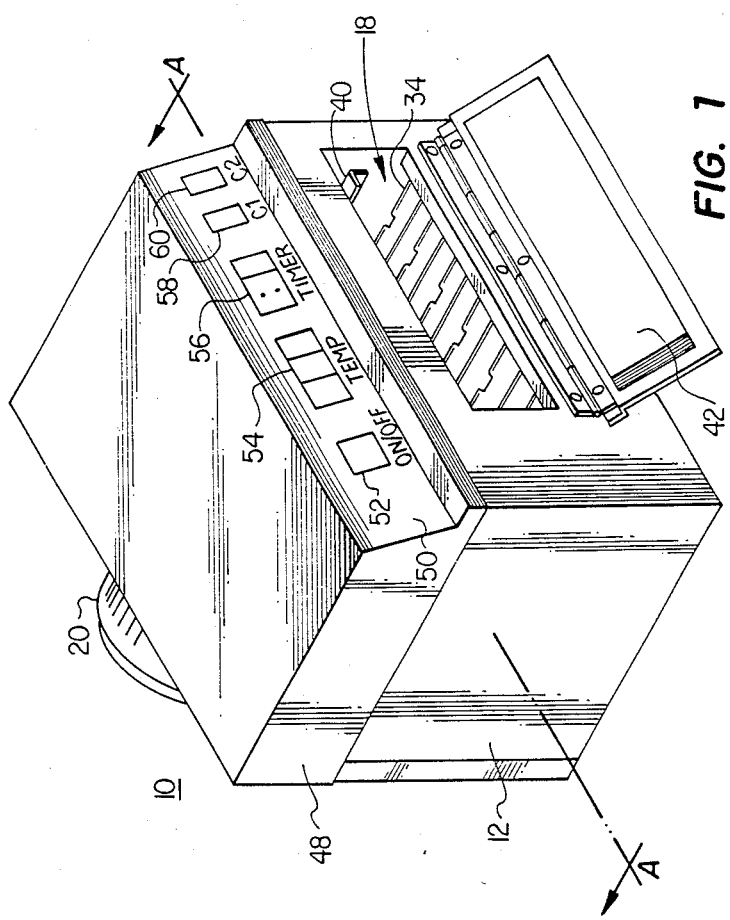
FIG. 1 is an isometric view of a preferred embodiment of the recirculating high velocity hot air sterilization device of the present invention.

Referring now to the drawings and, in particular, FIG. 1, a preferred recirculating high velocity hot air sterilization device generally indicated at 10 is defined by an enclosure or housing 12. As shown more clearly in FIG. 2, the enclosure 12 includes a plurality of walls 14. Walls 14 are preferably insulated. A partition 16 divides the enclosure 12 into a sterilization chamber 18 and a plenum chamber. A blower 20 is disposed within the plenum chamber of enclosure 12. The intake port 22 of blower 20 is in fluid communication with sterilization chamber 18. The outlet port 24 of blower 20 is in fluid communication with a duct chamber 26. A wall 27 separates the duct chamber 26 from the sterilization chamber 18. An airflow opening 28 is provided within wall 27 to allow for fluid communication between duct chamber 26 and sterilization chamber 18.

Figure 2:
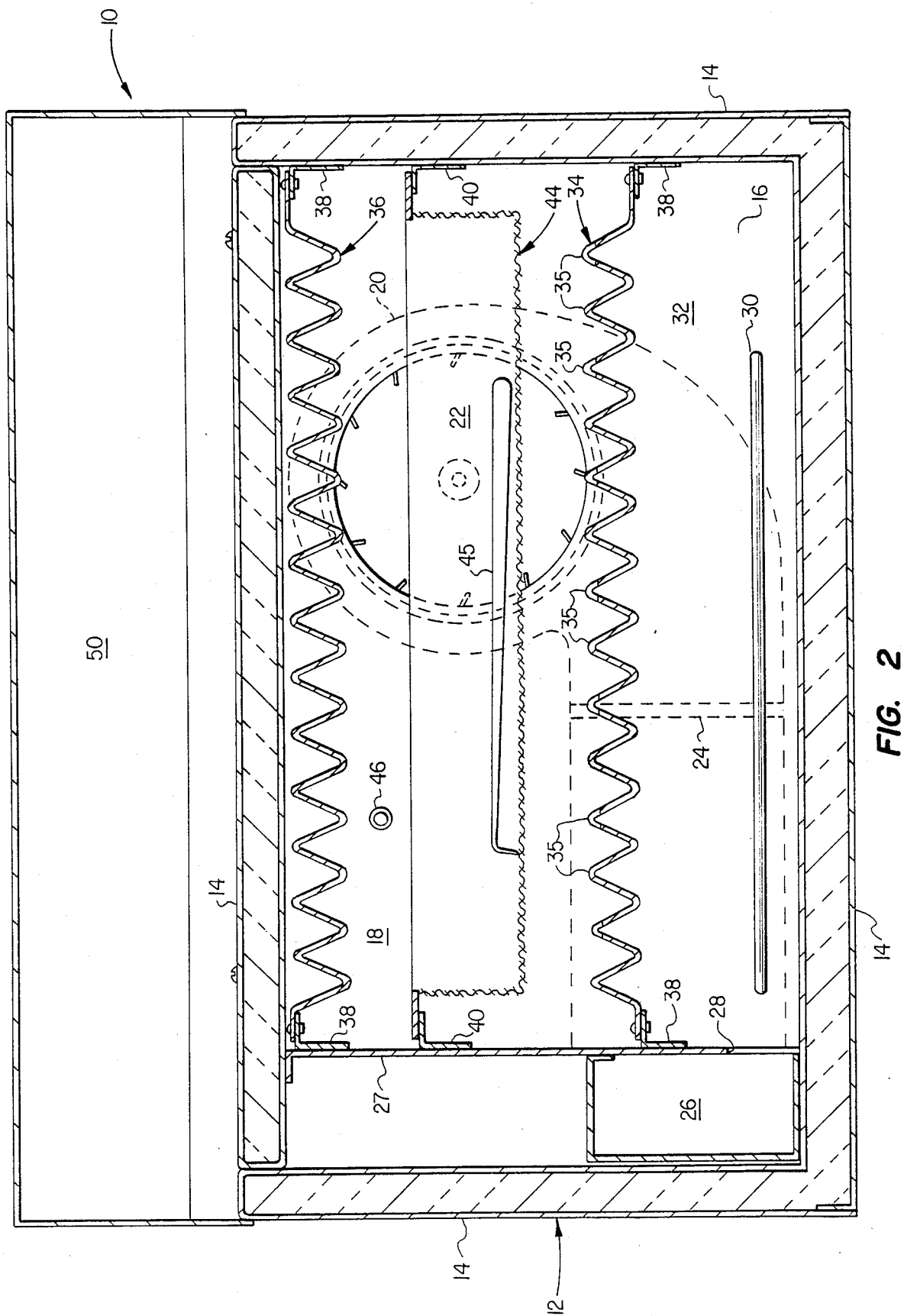
FIG. 2 is a cross-sectional view of the recirculating high velocity, hot air sterilization device of the present invention.

As shown in FIG. 2, a perforated jet curtain plate 34 is provided within enclosure 12. The perforated jet curtain plate 34 partially defines an air supply plenum 32 within sterilization chamber 14. A heating element 30 is provided within plenum 32 to heat the air entering the plenum through air flow opening 28. An upper non-perforated jet curtain or air deflector plate 36 may preferably be disposed within sterilization chamber 18. The perforated jet curtain plate 34 and non-perforated jet curtain plate 36 are rigidly supported within enclosure 12 by a plurality of support flanges 38. A plurality of support flanges 40 are provided between perforated jet curtain plate 34 and non-perforated jet curtain plate 36 to removably support an open wire mesh tray 44 containing metal dental or surgical metal instruments 45. A door 42 (FIG. 1) is openable to provide access to sterilization chamber 18. Door 42 provides an air-tight seal and serves to seal the sterilization chamber 18 from the outside environment.

The perforated jet curtain plate 34 (FIG. 2) is mounted within housing 10 and is spaced apart from and above the heating element 30, and downwardly from the upper plate 36. The perforated jet curtain plate 34 contains an array of elongated, generally rectangular slots 35 through which turbulized air from the air supply plenum 32 is unturbulized and directed in a series of heated air impingement jets toward the dental or surgical metal instruments 45 supported in tray 44. The rectangular slots 35 of the perforated jet curtain plate 34 vary in width, length and number in relation to the horsepower of the blower to yield jets of air emanating from the slots 35 at a velocity of from 1500 to 3000 feet/minute. The velocity of air emanating from the slots 35 may be measured by a Dwyer Air Velocity Calculator: #460 Air Meter made by Dwyer Instruments, Inc., Michigan City, Ind. under U.S. Pat. No. 2,993,374. The velocity of the air emanating from the slots 35 depends upon the ratio of the area of the output port 24 of the blower 20 to the area of the slots 35. The velocity of the air emanating from the slots 35 also depends upon the horsepower and speed of the blower 20. Those skilled in the art will recognize that these variables may be adjusted through routine experimentation to achieve a desired velocity of air emanating from the slots 35.

The perforated jet curtain plate 34 distributes heat uniformly and efficiently to the instruments 45 being supported and sterilized in the tray 44. The deturbulized air emanating from the slots 35 of the perforated jet curtain plate 34 travels through the sterilization chamber 18, past a thermocouple 46 for sensing the temperature of the hot air to the corrugated, non-perforated jet curtain plate 36. The curtain plate 36 reflects the hot air rearwardly to the blower. The air is then circulated back through the blower 20 to again enter the duct chamber 26, the air supply plenum 32 and the sterilization chamber 18, in sequence. When the blower 20 is operating, a continuous stream of air flows through the entire system. Turbulized air from the blower 20 scrubs the heating element 30 and picks up heat which is then delivered to the instruments by the high velocity jets of air emanating from the slots 35 of the perforated jet curtain plate 34.

The perforated jet curtain plate 34 is uniquely corrugated in a pattern of rounded v-shaped corrugations alternately v-shaped and inverted v-shaped. The slots 35 of the perforated jet curtain plate 34 are disposed in the crests rather than the troughs of the v-shaped corrugations.

The extreme efficiency of jets of high velocity heated air emanating from the slots 35 of the perforated jet curtain plate 34 speeds the sterilization and depyrogenation of the dental or surgical metal instruments supported in the tray 44 without requiring an extreme differential between the temperature of the heating element 30 and the temperature of the air. Unused heat contained in the recirculating air is conserved by the device of the present invention which, as noted previously, may be insulated to reduce heat loss. It is therefore possible to provide quick efficient sterilization and depyrogenation of dental or surgical metal instruments with air heated to about 350° to 400° F., and preferably about 375° F., without requiring the heating element 30 to run at full capacity, which conserves energy and increases the life of the instruments. It is well known by those skilled in the art that the alloy arrangements in dental and surgical metal instruments are disrupted when exposed to temperatures in excess of 400° F.

A control chamber 48 (FIG. 1) is located above the sterilization chamber 18 for housing the controller system circuitry hereinafter described in detail. A control panel 50 is disposed on the external portion of the control chamber 48. The control panel 50 includes an on/off switch 52, a temperature display 54, a timer display 56, and cycle 1 and cycle 2 selection switches 58 and 60.

Figure 3C:
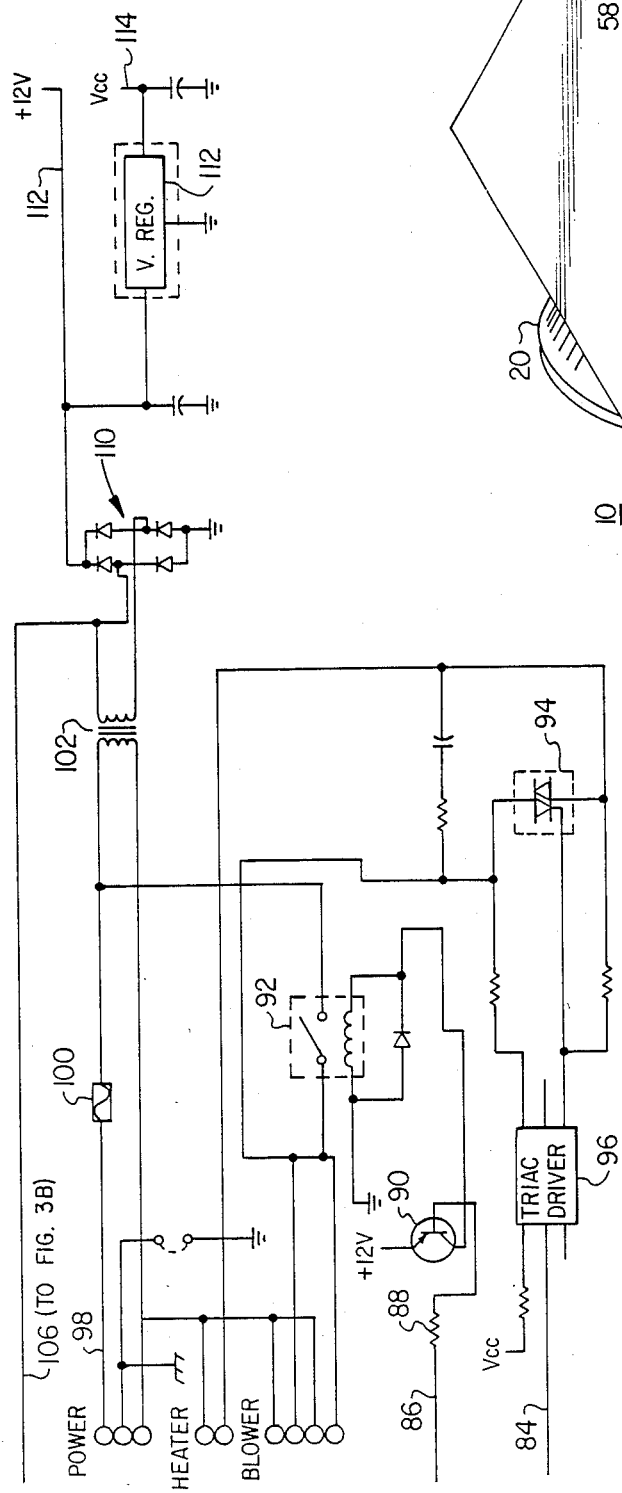
FIGS. 3a-3e constitute a schematic view of the controller for the recirculating high velocity hot air sterilization device of the present invention.
Figure 3A:
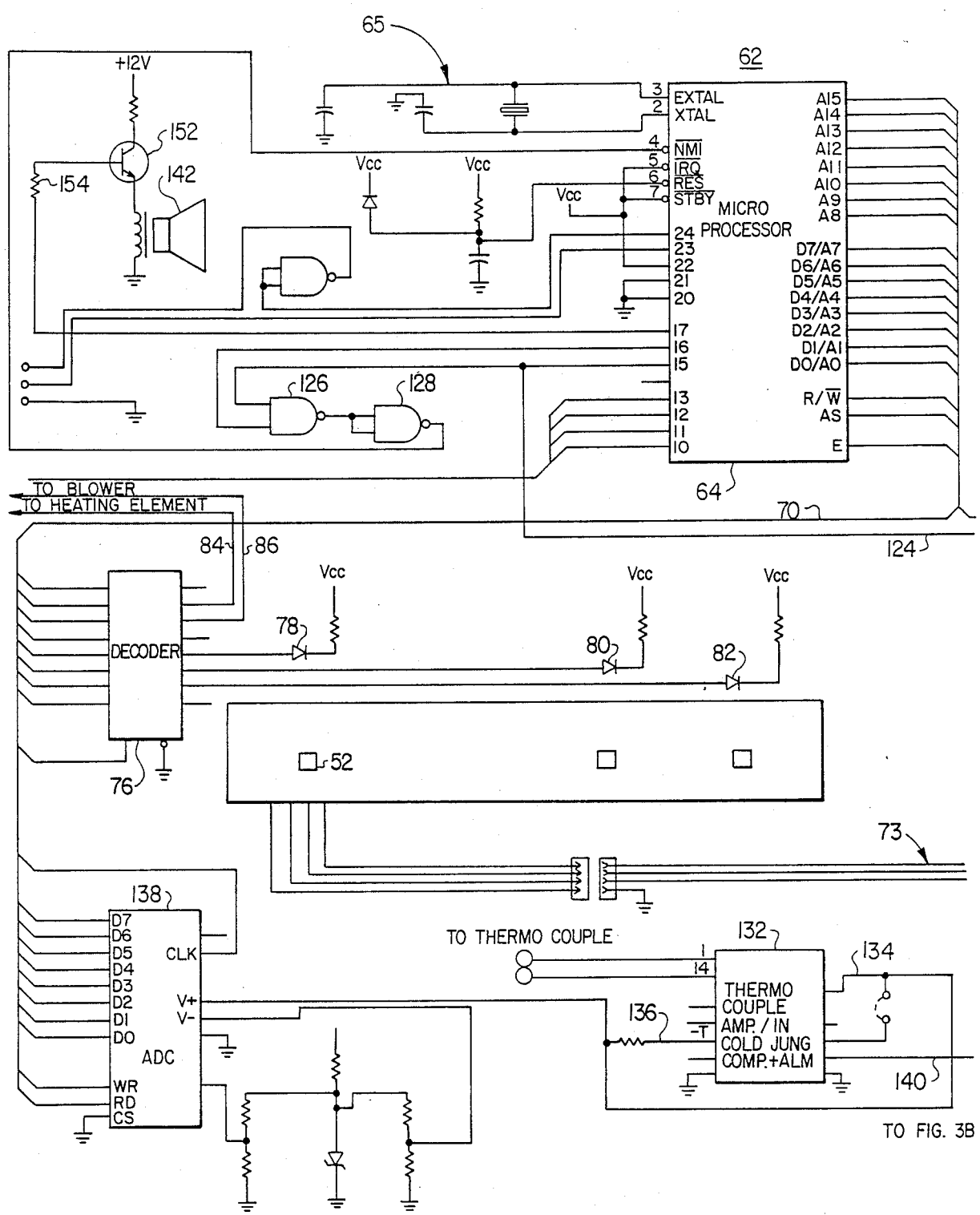

Referring now to FIGS. 3a-3e, the controller system includes a processor means (FIG. 3a). The processor means 62 includes a microprocessor 64 such as, for example, an 8-bit HD63B03 microprocessor sold by Hitachi, Ltd. The microprocessor 64 has a plurality of input terminals and address and data output terminals for providing an interface to circuits hereinafter described, a test console port, a small amount of random access memory (RAM) for data storage, and a very accurate crystal based timing circuit 65 for checking the natural timer hereinafter described. A typical address decoder which includes a demultiplexer decoder 66 (FIG. 3b) and a latch 68, is attached to the address and data output terminals by a data and address bus 70 for processing 16 bit addresses and 8 bit data words. And an electrically programmable read only memory (EPROM) 72, which contains the operating instruction software, is connected by the data and address bus 70 to the microprocessor for controlling the operation of the microprocessor. The display 56 completes the processor means 62.

Figure 3B:
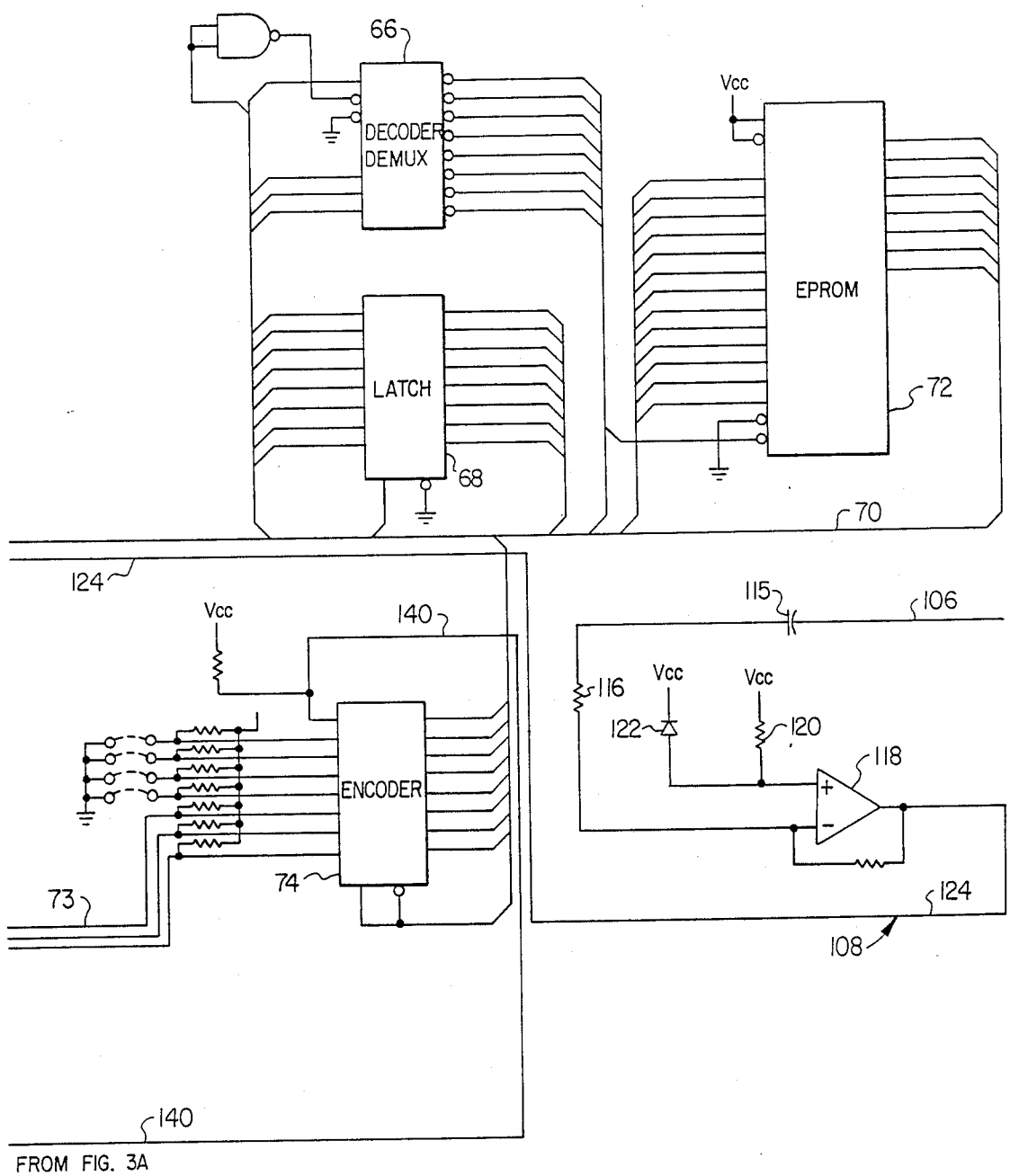
Figure 3D:
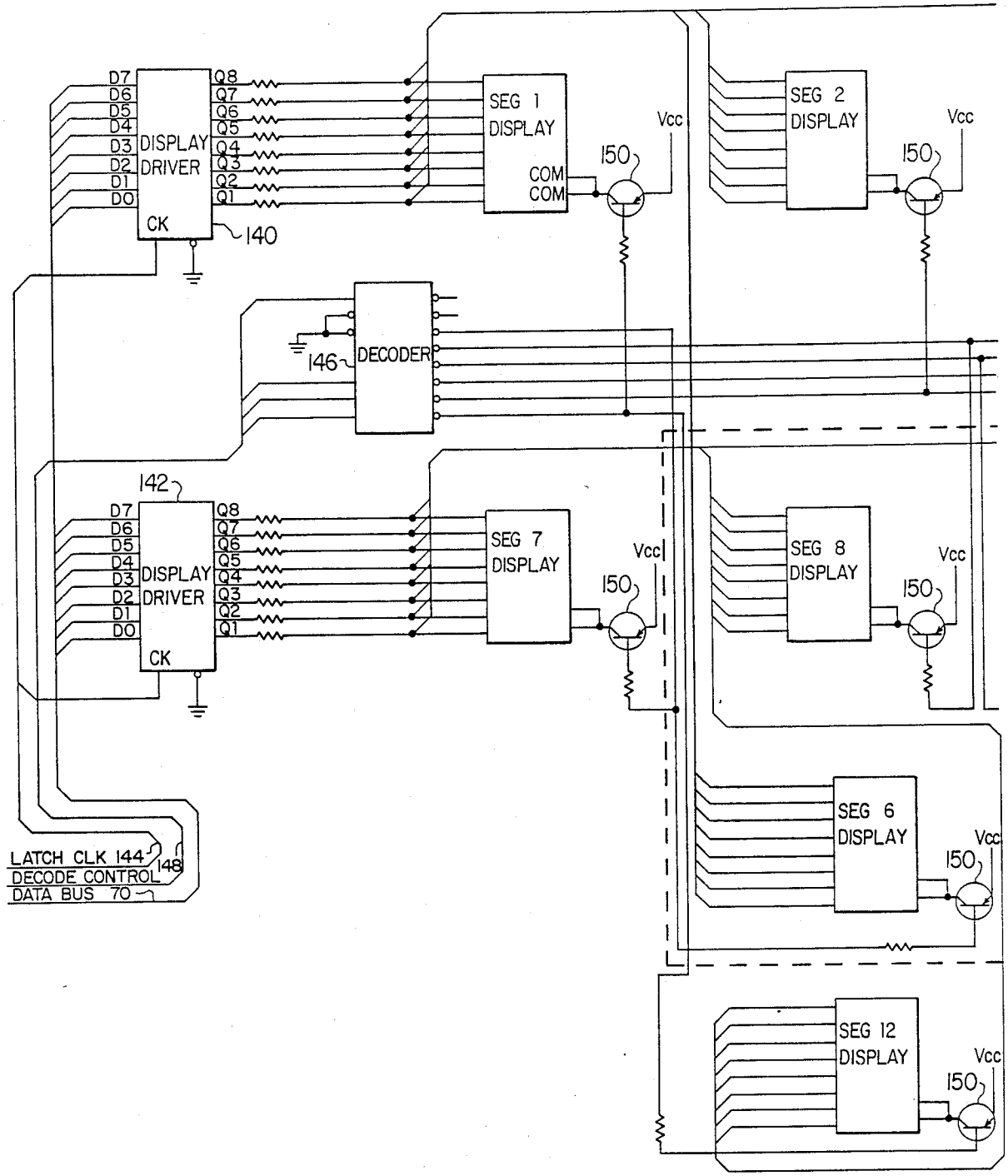
Figure 3E:
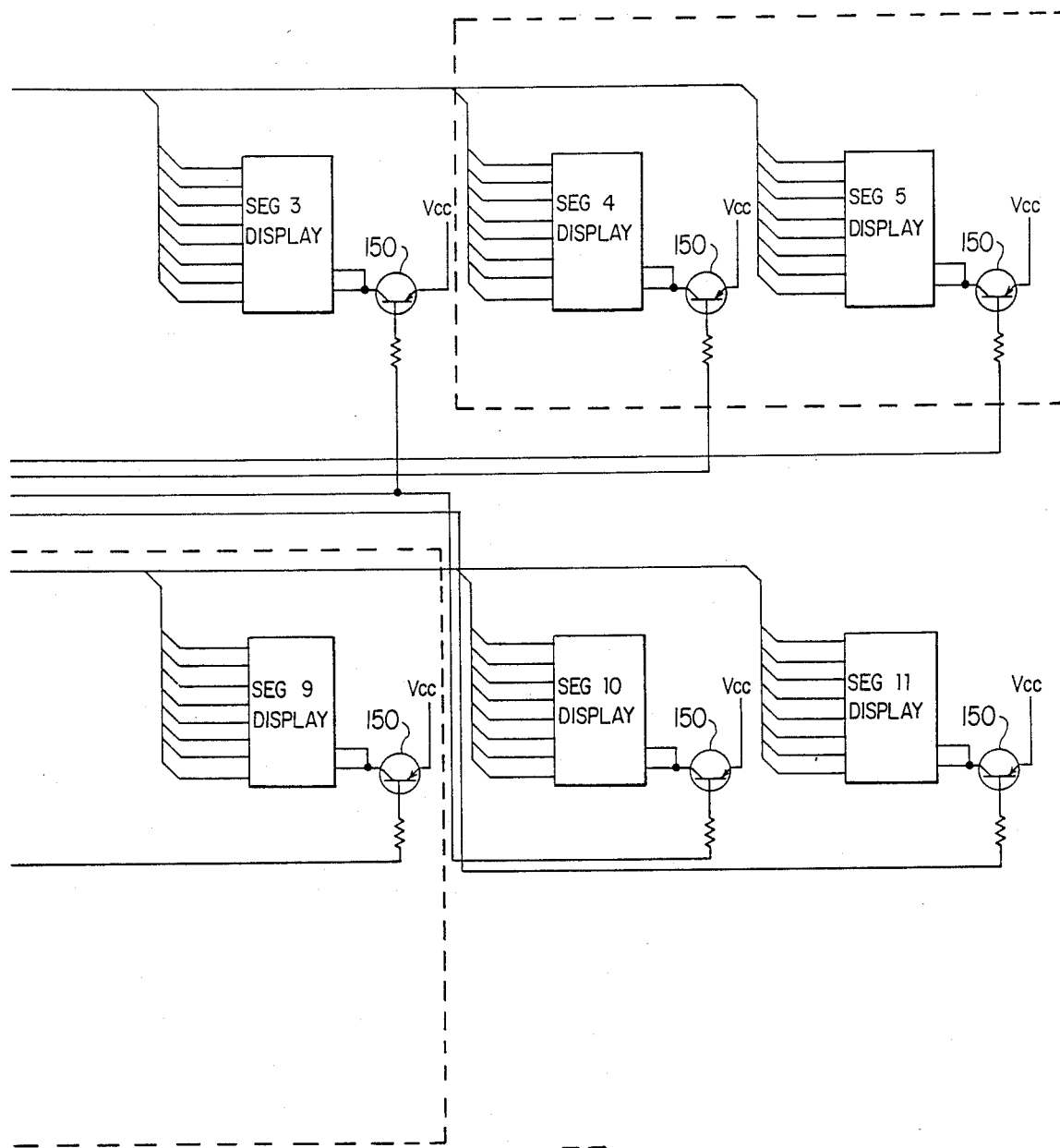

The on/off switch 52 (FIG. 3a) is connected by leads 73 to an encoder 74 (FIG. 3b). The encoder 74 is connected by the data and address bus 70 to the microprocessor 64 (FIG. 3a). The microprocessor monitors the position of the on/off switch and outputs coded signals on data and address bus 70 to a decoder 76. The decoder 76 has output terminals connected respectively to three light emitting diodes 78, 80, and 82 for indicating, respectively, the on/off switch status and cycle 1 or cycle 2 selection, and by leads 84 and 86 to a blower power control circuit (FIG. 3c) and to a heating element power control circuit for controlling the connection of ac power to the blower 20 and heating element 30 (FIG. 2).

The blower circuit includes a bias resistor 88 (FIG. 3c) having one end connected by lead 86 to the decoder 76 and a second end connected to the base of a power transistor 90. When a switch on indicating signal is applied to the base of the transistor 90, the transistor turns on to close a relay switch 92 and supply working power from a source thereof to the blower 20 and to a TRIAC 94 or other suitable thyristor of the heating element circuit.

The heating element circuit includes a TRIAC driver 96 having an input connected by lead 84 to the decoder 76 and an output connected to the gate of the TRIAC 94. The TRIAC when triggered on supplies power to the heating element 30. The relay switch 92 provides on/off control of the blower as well as safety control of the heater, and the TRIAC provides proportional control of the heater with an opto-coupler to isolate the logic control from the ac power.

A power supply circuit includes a power connector 98 for connection to a typical 50 or 60 Hertz power line. A thermal fuse 100 is connected between the connector 98 and junction of the blower circuit relay 92 and a transformer 102. The transformer output, which is for example, a 12Vac output is connected to the junction of lead 106 to a 12Vac zero detector circuit (FIG. 3b) and a full wave rectifier 110 (FIG. 3c). The full wave rectifier is connected to the transformer for converting the ac transformer output to dc of a first voltage (12V). The 12V output of the full wave rectifier is connected to the junction of terminal 112 to power the relays and an audible alarm hereinafter described, and a voltage regulator 112. The voltage regulator converts the +12Vdc to a second voltage (+5V Vcc) for output at terminal 114 to the microprocessor, display and temperature sensing electronics.

The zero detection circuit 108 (FIG. 3b) includes a filter 115 connected by lead 106 to the output of transformer 102 for removing any dc component and to voltage dropping resistor 116. The dropping resistor 116 is connected to the negative terminal of comparator 118. The positive terminal of comparator 118 is connected to the junction of a resistor 120 and diode 122 connected to the Vcc source for receiving a voltage stabilized Vcc. The output of the comparator 118 is connected by lead 124 to the junction of pin 15 of the microprocessor 64 (FIG. 3a) and first terminal of a NAND gate 126. The second terminal of NAND gate 126 is connected to output pin 16 of the microprocessor. A second NAND gate 128 has its input terminals connected to the output of NAND gate 126 and its output connected to the nonmaskable interrupt pin 4 of the microprocessor. Thus, the zero crossing detector provides basic timing to the processor based on the 50 or 60 Hz cycle of the ac line for synchronizing the TRIAC operation.

A temperature sensor electronic circuit 130 (FIG. 3a) includes a thermocouple amplifier 132 with cold junction compensation having input terminals connected to the temperature sensing thermocouple 46 mounted in the sterilization chamber 18. A suitable thermocouple amplifier with cold junction compensation is an AD 595 device manufactured by Analog Devices, Inc. The output of the thermocouple amplifier is connected by lead 134 to the junction of a feedback line 136 to the negative temperature terminal of the amplifier and to an analog to digital converter (ADC) 138. The thermocouple amplifier receives the output feedback and provides an offset adjustment to allow for re-calibration to the dynamics of the sterilizer's chamber. If the thermocouple is disconnected or out of limits the microprocessor generates an alarm signal back through lead 140 to the encoder 74 (FIG. 3b) and alarm speaker 142 (FIG. 3a). The ADC 138 converts the temperature indicating analog signals to digital signals for input to the microprocessor or 64.

The display (FIGS. 3d-3e) includes in addition to the three LED indicators 78, 80, and 82 (FIG. 3a), twelve seven segment displays and seven logic inputs. Of the twelve seven segment displays three are used to display temperature and three are used to display time remaining for either cycle 1 or cycle 2 operation hereinafter described, and the remaining displays are not used. The time displays are also used to show the last cycle completed and any error codes. For a timing cycle longer than 9 minutes and 59 seconds, additional displays can be installed. Of the seven logic inputs, three are used for front panel switches and four are used for on-board jumper options. The display is connected directly to the microprocessor 64 and provides no action on its own. The functionality of the switches and displays are under the sole control of the microprocessor.

The display includes display drivers 140 and 142 having their clock terminals connected to the latch clock signal line 144 of the microprocessor 64, and their data input terminals connected to the microprocessor 64 through the data bus 70. A decoder 146, is connected to the microprocessor decode control line 148 of the microprocessor. The display drivers 140 and 142 have their output terminals connected to the input terminals of six of the twelve seven segment display modules (FIGS. 3d and 3e), and the decoder 146 has its outputs connected respectively to the bases of transistor switches 150 for the display elements. Each output of the decoder is connected to bases of the transistors 150 for two displays and act as switches for connecting Vcc to the displays.

Returning to the microprocessor 64 (FIG. 3a), a speaker circuit includes a transistor 152 having its base connected to output pin 17 through a bias resistor 154. The transistor 152 is biased on to supply the positive operating voltage (+12V) to a speaker 142 for purposes hereinafter described.

In operation the unit 10 is connected to a power source by connector 98 and the microprocessor 64 is powered up with instructions to scan the on/off switch. Turning the on/off switch on is detected by the microprocessor. The microprocessor then receives instructions to activate the blower, heater, display and enable the two cycle select switches. If the unit was on and no cycle activated, the unit receives instructions to shut off the display, cycle switches and heater immediately, and to shut off the blower after the temperature sensed has dropped below a preset value for a pre-set time. Activation of the cycle switches enables the microprocessor to cycle through the prescribed temperature and time instructions, sound the alarm and display the cycle that has been completed. During the on time the microprocessor receives instructions to continuously display the updated temperature, and during a cycle to display the time remaining in the cycle.

The processor ensures that a cycle is completed only if the temperatures were maintained continuously for the prescribed times. If during the cycle the temperature drops below the minimum sterilization temperature preferably 375 degrees Fahrenheit, the microprocessor receives instructions to automatically restart the cycle. The operator sees a continuous display of full time remaining as long as the sterilizer is below temperature. The time remaining display would start decrementing as soon as the operating temperature is reached.

The microprocessor instructions are broken up into a main program loop, an NMI interrupt based on the ac cycle, a quadrature interrupt from the crystal based timer and service routines based on a one second timing tick.

The main program loop provides a self check and initialization when it is plugged in. The display indicators and beeper are tested at turn on. All indicators and the beeper are turned on for a few seconds to allow the operator to verify their working. The operator must note if any segment has burned out. The main program loop also times the zero crossing to determine if it is on a 50 or 60 Hz system and sets up accordingly. The unit then sits idle scanning only the on/off switch. The unit again does a self check when the on/off switch is pressed. This includes a check sum verification of the operating software, exercise check, and clearing of the local data store RAM and in addition to the original power up tests turns on all indicators and displays for a few (five) seconds as a check for burned out elements.

The main loop then turns the fans and the heaters fully on, enables the heater control software and the display software, and scans for keyboard inputs and alarms. The main loop reads the processed temperature value and converts it to display format, sets the cycle times according to switch activation and the interlock of cycles. The main loop also provides warble generation, switch debounce and shut down sequence including either holding the blower on until the oven temperature is below a preset value or holding the blower on for a preset time.

The nonmaskable interrupt (NMI) routine provides a timing reference point for each ac cycle of the 50 Hz or 60 Hz ac power going to the heaters. This is required as the proportional control of the heaters is achieved by turning on the TRIAC for a preselected fraction of the ac cycle. The TRIAC naturally turns off at every zero crossing in the cycle; thus, the reference of the turn on pulse to the cycle zero crossing is very important. The interrupt for triggering the TRIAC on handler resets the time interrupt for triggering the TRIAC on so the quadrature interrupts must be tied to the cycle zero crossing. A phase relationship between these two (NMI and TI) interrupts is established at this point based on the duty cycle requested by the heater control software. That is, the switch 92 after initialization is continuously supplying an ac working current to the blower and TRIAC. A TRIAC is a semiconductor device that snaps to a completely on state for working current when a momentary pulse of control current is received and can be turned off only by interrupting the working current elsewhere in the circuit. As the working current is ac it goes off twice each ac cycle (at the 180 and 360 degree zero current crossing points) or for 60 Hz ac 120 times a second. The zero crossing detector is detecting the 120 zero current crossings each second and its logic is applying an outside pulse to the nonmaskable interrupt (NMI) terminal of the programmable controller.

The NMI interrupts the main program of the programmable controller 120 times a second and each time calls up the interrupt handler program. The interrupt handler program during heat up to the sterilization temperature pulses the TRIAC back on each time it goes off to provide working current to the heater element substantially continuously to provide a 100% duty cycle. After heat up, the interrupt handler computes a duty cycle for the heater for use during each second of heater operation.

The duty cycle is sufficient to maintain substantially constant the sterilization temperature during this time. The interrupt handler using the duty cycle information determines the quadrant and time to issue a turn on pulse to the TRIAC in order that the duty cycle will terminate on the 360 degree zero crossing of each ac cycle. After pulsing on the TRIAC to start a duty cycle the interrupt handler issues an instruction to pulse the TRIAC back on for any 180 degree crossing occurring during the duty cycle and an instruction not to send a turn on pulse to the TRIAC at the 360 degree crossing. Thus, the TRIAC remains off until triggered on again at the beginning of the next duty cycle.

The NMI is also used to provide real-time counters for all timing functions since the 50/60 Hz timing is very accurate. The thermocouple is also read during this ac cycle and accumulated in an average.

The quadrature interrupts are actually initiated by the zero crossing of the ac cycle, and break the ac cycle into four evenly timed quadrants.

The quadrant when the TRIAC is triggered by the time interrupt provides a coarse control of the heater power and the phase relationship to the NMI zero crossing interrupt provides the fine adjustment. The TRIAC is fired on entering this routine if it is the right quadrant and the heaters are enabled. This routine also provides a predictor function for the NMI zero crossing that blocks spurious interrupts and inserts missing cycles.

The one second based timing service routines are implemented as a cycle count of the zero crossing NMI interrupt. They decrement any timers that have been activated by the main loop software. They also update the current oven temperature by averaging the accumulated 50 or 60 readings and clearing an accumulator to form the next average. This current oven temperature is used for the temperature display as well as the proportional heater control. The proportional heater control software calculates the quadrant and the phase relationship to be used by the quadrature interrupt handlers in driving the TRIAC for the next second.

A short history is also kept of the temperature to be used in calculating the first and second derivatives of temperature with respect to time. The control equation is based on a straight forward second order equation using the difference between current and required temperatures and its derivatives. There are some discontinuities in the control function to try to compensate for previous history of abnormalities. The processor receives instructions to turn off the complete system should the temperatures exceed a certain level based on the assumption that the TRIAC has failed. The processor also looks at the history of temperatures and duty cycles to determine if the door has been open for a long time or that the heater chamber may be super heated. The microprocessor receives instructions to either cut back or step up the duty cycle according to the past history. These discontinuities are intended to speed up the rise to operating temperature and reduce overshoots by predicting abnormalities. Assuming there are no abnormal temperature jumps, the second order equation alone provides a smooth control of the heaters at operating temperatures.

The display is multiplexed in the sense that only two digits are displayed at any one time. This saves hardware and power. The illusion that there is a steady display of up to twelve digits is achieved by quickly displaying the six pairs that form the twelve digits, each in turn. The quadrature interrupt initiates the display of the next pair. This interrupt is running at, for example, $4 \times 60 = 240$ or $4 \times 50 = 200$ times a second thereby making the display look stationary. If the ac cycle were not broken up in this way, the display update of 60 times a second would be too slow and the display would appear to flicker.

Four basic error code groups are implemented by the processor. The error codes are displayed in the time window and have the following general format 'E-XY' where 'E' is a fixed format to identify this as an error display, the 'X' identifies the error group and the 'Y' identifies the error within the group. All errors will cause the microprocessor to turn off the TRIAC control to the heater and the relay controlling all ac power devices. Thus, the blower as well as the heater will be shut off. The error code flashes and the beeper sounds in time to the flashing display. The temperature will continue to show the current temperature; however, this reading may be false depending on the error type. The unit will remain in this state until the operator turns off the unit with the on/off switch or disconnects the power cord.

The on/off switch disables the beeper and the error code is displayed continuously instead of flashing. Unplugging the unit resets the error detect logic and the unit will start as if there were no error when it is plugged back in. Should the error code be detected again then it will go into the error state again as described above. The error codes are as follows:

Processor Failures:

E-10—EPROM Checksum failure (verifies program code not changed)
E-11—RAM failure (verifies variable space working)
E-12—Switch failure (verifies switches not shorted)
E-13—Timing failure (verifies 50-60 Hz line timing against on-board crystal)

Temperature Probe:

E-20—OPEN probe (check for broken leads)

E-21—REASONABLENESS check (check for rapidly changing or erratic temperature readings)

Heat Drive:

E-30—OVER heat (check for blower failure or shorted TRIAC)

E-31—UNDER heat (check for burnt out heater element).

The software program for accomplishing the above described features of the invention is contained in the file wrapper for those persons skilled in the art desiring more detailed information as to how to implement these features.

Although only a single embodiment of the invention has been described, it will be apparent to those persons skilled in the art that various modifications to the details of construction shown and described can be made without departing from the scope of the invention.

What is claimed is:

1. An automatically controlled sterilization device for nondestructively sterilizing medical instruments comprising:

a sterilization chamber, a temperature sensing means mounted in the sterilization chamber for outputting temperature indicating signals;

a plenum chamber, a blower means and a heater means mounted in operative association in the plenum chamber, for forcing hot air into the sterilization chamber;

a control chamber, a programmable controller means mounted in the control chamber for controlling operation of the sterilization device at a sterilization temperature between about 350° F. and 400° F.;

an on/off switch means connected to the programmable controller for initializing the sterilization device; and an ac circuit means for connection to a source of ac power, said ac circuit means including a thyristor connected to the heater means, a switch means connected to the blower means and thyristor, said thyristor having a triggeriing gate for selectively pulsing on the thyristor, an ac zero crossing detector means connected to the ac power source for determining zero crossings for each ac cycle, and logic means connected to the zero crossing detector means for producing interrupt signals for the programmable controller indicative of zero current crossings and corresponding turn off of the ac working current; and wherein the programmable controller includes: a first instruction means including means for monitoring the on/off switch means for selectively supplying ac working current to the blower means and thyristor, a nonmaskable interrupt means responsive to the interrupt signals of the logic means for interrupting the first instruction means for said second instruction means, a second instruction means including an ac working current duty cycle determining means connected to the temperature sensing means for producing working current duty cycle information first for a 100% duty cycle for minimizing the time required to raise the temperature in the sterilization chamber up to a selected sterilization temperature and thereafter to maintain the temperature, timing means responsive to the zero crossing interrupts and duty cycle information for determining ac cycle quadrants and time to issue a control pulse to the thyristor's triggering gate for enabling the thyristor to begin each ac working current duty cycle at a time for enabling completion of the duty cycle on the last zero crossing of each ac cycle, and means for determining any zero crossings occurring during a duty cycle and responsive to corresponding interrupts therefor for pulsing the triggering gate to turn the thyristor back on, whereby the thyristor is triggered on by the timing means timing pulse and remains in until the working current is interrupted at the end of the duty cycle and the thyristor is automatically reset to the off state.

2. An automatically controlled sterilization device according to claim 1, wherein the programmable controller further includes a timing means and means for setting the timing means selectively for first timing cycle 1 or cycle 2 and means connected to the alarm 3. An automatically controlled sterilization device according to claim 1 further including first timing cycle 1 and second timing cycle 2 operation selection switches and wherein the programmable controller further includes means responsive to the cycle 1 and cycle 2 operating selection switches for selectively setting first and second sterilization temperatures.

4. An automatically controlled sterilization device according to claim 1, wherein the programmable controller includes means responsive to the temperature sensing means for restarting the timer whenever the temperature of the sterilization chamber falls substantially below a preselected sterilization temperature.

5. An automatically controlled sterilization device according to claim 2 further including an alarm means, and wherein the programmable controller further includes means connected to the timing means for determining the completion of either sterilization timing cycle 1 or cycle 2 and means connected to the alarm means for sounding the alarm at the completion of the sterilization cycle 1 or cycle 2.

6. An automatically controlled sterilization device according to claim 1, wherein the programmable controller includes error detecting means for determining errors selected from the group, consisting of programmable controller failures, temperature failures and heater drive failures, said heater drive failures including means connected to the temperature sensing means for detecting under heating conditions, and means for detecting over heating conditions, means for turning off the power to the heating element and blower, and means for displaying error codes including for over heating a code for checking for blower failure or shorted ac power switching means, and for under heating for checking the heater element for burnout.

7. An automatically controlled sterilization device according to claim 1 wherein the sterilization chamber has a support means and an outlet in open communication with the plenum chamber for creating a recirculating flow of air which is flowed through the sterilization chamber in a manner maintaining a substantially uniform air temperature and flow distribution throughout said sterilization chamber, and for causing a portion of the recirculating air traversing said sterilization zone to impinge upon an object in the support means at a velocity sufficient to significantly accelerate heat transfer from the air to the supported object.

8. The apparatus of claim 7 wherein:

said sterilization chamber includes means for creating a recirculating flow of air and for causing a portion of the recirculating air traversing said sterilization zone to impinge upon the supported object wherein said flow recirculation means include a perforated wall member defining a boundary of said sterilization chamber through which said recirculating flow of air is delivered to said sterilization chamber in the form of a series of relatively high velocity air jets which traverse said sterilization zone.

9. The apparatus of claim 8 wherein:
said wall member is a corrugated plate member having ridges therein through which the perforations of said wall member are formed.

10. The apparatus of claim 9 wherein:
said perforations have generally rectangular shapes.

11. An automatically controlled sterilization apparatus for nondestructively sterilizing medical instruments comprising:
- a sterilizing chamber for medical instruments, a temperature sensing means mounted in the sterilizing chamber for producing temperature indicating signals;
- a blower means and a heater means in operative association with each other for injecting hot air into the sterilizing chamber for raising the temperature thereof to a sterilizing temperature between 350° F. and 400° F.;
- an on/off switch means for initializing the apparatus comprising first and second switching means, an ac power source, the source of power being connected through the first switching means to the blower means and second switching means and through the second switching means to the heater means, and an ac zero crossing detector means connected to the ac power source for generating signals indicative of the zero and 180 degree ac zero power points; and
- a programmable controller means including: a first control means having means for monitoring the on/off switch and powering on the first switching means for controlling the connection of ac working power to the blower means and to the second switching means; a duty cycle determining means responsive to the temperature indicating signals for selecting a corresponding working time for each ac cycle and determining a time to start the selected working time; an interrupt means reponsive to the zero power point indicating signals for interrupting the first control means for a second control means, said second control means having a timing means connected to the duty cycle determining means and interrupt means for receiving a first interrupt signal for starting the timing means while allowing the second switching means to remain off, and means responsive to the timing means reaching the starting time of a duty cycle for pulsing on the second switching means and thereafter during the working time when the second switching means goes off at each 180 degree zero ac power crossing point for pulsing on the second switching means to complete the selected working time at the zero degree zero crossing point.

* * * * *

UNITED STATES PATENT AND TRADEMARK OFFICE
CERTIFICATE OF CORRECTION

PATENT NO. : 4,923,681

DATED : May 8, 1990

INVENTOR(S) : M. Keith Cox et al.

It is certified that error appears in the above-identified patent and that said Letters Patent is hereby corrected as shown below:

ON TITLE PAGE:

In the References Cited, "8/1984 Payne" should be --4/1984 Payne--.

In the Abstract, line 6, "hor air" should be --hot air--.

Col. 1, lines 28-29, "that patient-s - not professionals acquire" should be --that patients - not professionals - acquire--.

Col. 9, line 29, "microprocessor or 64" should be --microprocessor 64--.

Col. 13, line 28, "chamber, for" should be --chamber for--.

Col. 14, line 10, "remains in until" should be --remains on until--.

UNITED STATES PATENT AND TRADEMARK OFFICE
CERTIFICATE OF CORRECTION

PATENT NO. : 4,923,681

DATED : May 8, 1990

INVENTOR(S) : M. Keith Cox et al

It is certified that error appears in the above-identified patent and that said Letters Patent is hereby corrected as shown below:

Col. 14, line 18, "1 or cycle 2 and means connected to the alarm" should be --1 and second timing cycle 2 sterilization periods--.

Col. 14, line 43, "group, consisting" should be --group consisting--.

Signed and Sealed this

Thirteenth Day of October, 1992

Attest:

DOUGLAS B. COMER

*Attesting Officer*   *Acting Commissioner of Patents and Trademarks*